United States Patent
Andresen et al.

(10) Patent No.: US 7,072,708 B1
(45) Date of Patent: Jul. 4, 2006

(54) DIFFERENTIATING ACUTE MYOCARDIAL INFARCTION FROM OTHER ECG ABNORMALITIES

(75) Inventors: Alan Andresen, McMinnville, OR (US); Rick Myers, McMinnville, OR (US); Camilo Bruce, Portland, OR (US); Ron Selvester, Long Beach, CA (US)

(73) Assignee: Inovise Medical, Inc., Portland, OR (US)

( * ) Notice: Subject to any disclaimer, the term of this patent is extended or adjusted under 35 U.S.C. 154(b) by 0 days.

(21) Appl. No.: 10/726,064

(22) Filed: Dec. 2, 2003

Related U.S. Application Data (60) Provisional application No. 60/430,462, filed on Dec. 2, 2002.

(51) Int. Cl.
*A61B 5/04* (2006.01)
(52) U.S. Cl. ............... 600/509; 600/517
(58) Field of Classification Search ........ 600/509, 600/512, 517
See application file for complete search history.

(56) References Cited

U.S. PATENT DOCUMENTS

| | | | |
|---|---|---|---|
| 4,896,677 A * | 1/1990 | Kaneko et al. | 600/509 |
| 5,003,983 A * | 4/1991 | Dingwall et al. | 600/517 |
| 5,456,261 A * | 10/1995 | Luczyk | 600/515 |
| 5,891,047 A * | 4/1999 | Lander et al. | 600/516 |
| 6,038,469 A * | 3/2000 | Karlsson et al. | 600/512 |
| 6,112,116 A * | 8/2000 | Fischell et al. | 600/517 |
| 6,115,628 A * | 9/2000 | Stadler et al. | 600/517 |
| 6,272,379 B1 * | 8/2001 | Fischell et al. | 607/5 |
| 6,339,720 B1 * | 1/2002 | Anzellini et al. | 600/517 |

* cited by examiner

*Primary Examiner*—Angela D. Sykes
*Assistant Examiner*—Lenwood Faulcon, Jr.
(74) *Attorney, Agent, or Firm*—Jon M. Dickinson PC; Robert D. Varitz PC (57) ABSTRACT

A method in a computer system for detecting myocardial infarction including the steps of (a) receiving ECG data, (b) analyzing that data for the presence of benign ST data, and (c), when the ST data is not benign, (1) establishing a pathological threshold, (2) normalizing any deviation in the ECG data, (3) applying a pattern analysis to the normalized ECG data, and (4) generating a score indicating the presence of a myocardial infarction based on the pattern analysis and the threshold.

1 Claim, 8 Drawing Sheets

DIFFERENTIATING ACUTE MYOCARDIAL INFARCTION FROM OTHER ECG ABNORMALITIES

CROSS-REFERENCE TO RELATED APPLICATION

This application claims the benefits of the following provisional application U.S. Patent Application 60/(430,462), filed on Dec. 2, 2002, entitled "DIFFERENTIATING ACUTE MYOCARDIAL INFARCTION FROM OTHER ECG ABNORMALITIES" and hereby incorporated by reference.

BACKGROUND AND SUMMARY OF THE INVENTION

The detection of acute MIs using ECGs is standard practice. The problem is that current approaches give poor performance. The performance is especially poor for patients with other anomalies such as LVH or conduction defects. The work included here encompasses new methods used in detecting acute MIs. Focus is on areas where current algorithms are deficient.

DETAILED DESCRIPTION OF THE DRAWINGS AND THE INVENTION

Acute Myocardial Detection

Figure 1:
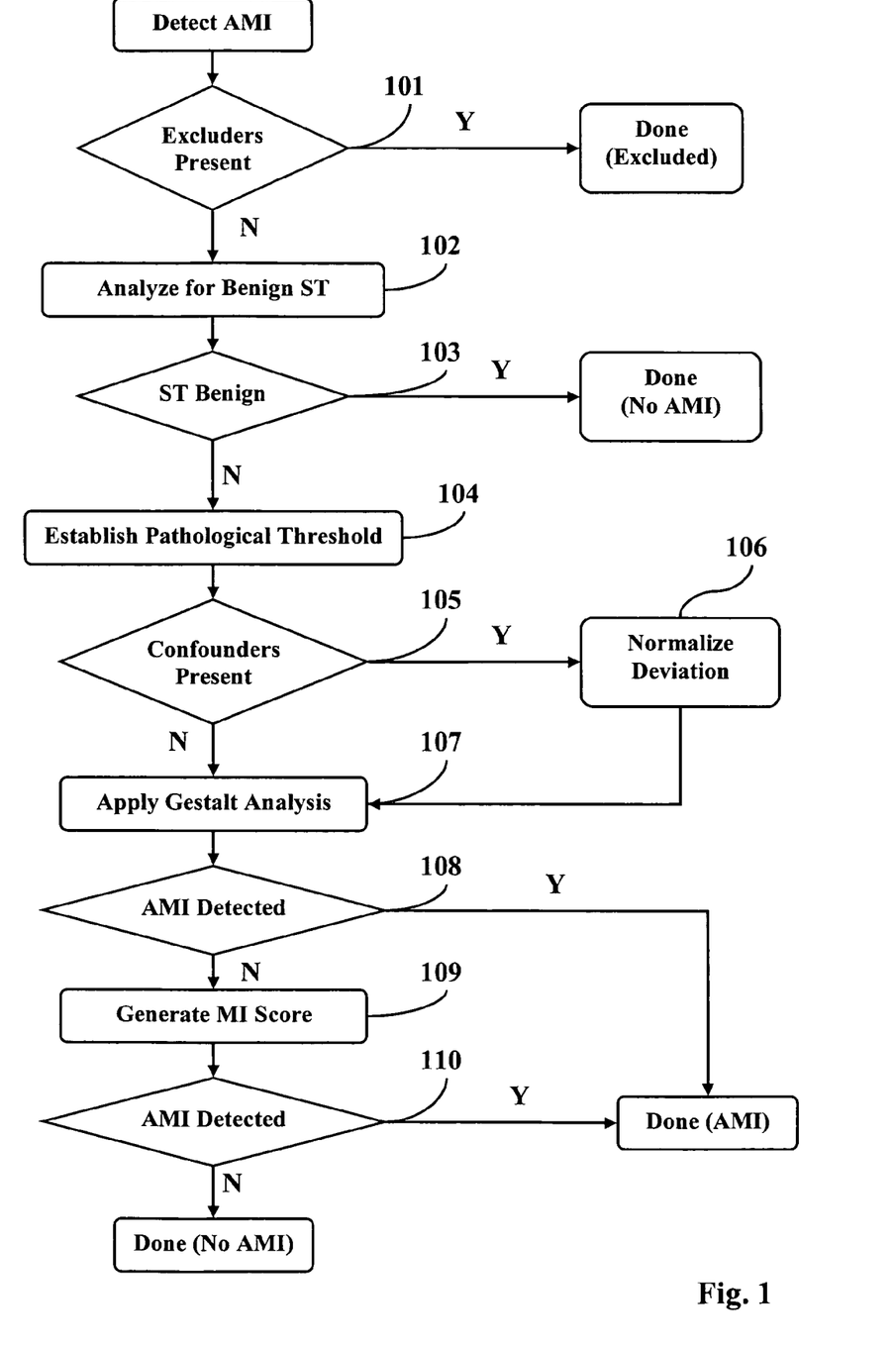

FIG. 1 is a flow diagram illustrating the processing of the detect AMI component in one embodiment. In decision block 101, if excluding conditions are present in the patient, then the component returns an indication that AMI cannot be detected, else the component continues at block 102. In block 102, the component analyzes the ECG data to determine whether the ST deviation is benign. The ST deviation may be benign because of the benign early repolarization or diffuse benign ST deviation. Because the component identifies benign ST deviation at this point, the algorithm for detecting AMI need not account for the presence of benign ST deviation. In decision block 103, if the ST deviation is benign, then the component returns an indication that no AMI has been detected, else the component continues at block 104. In block 104, the component establishes various pathological thresholds based on gender, race, age, confounding conditions, and so on. These thresholds are used when generating a score indicating the presence of AMI. In decision block 105, if any confounding conditions are present in the patient, then the component continues at block 106, else the component continues at block 107. In block 106, the component normalizes the ECG data to account for the deviations resulting from the confounding conditions. The confounding conditions may include LVH, RVH, LBBB, RBBB, and LAFB. For example, a certain blockage may result in ischemia whose effect on the ECG can be removed. In block 107, the component applies a pattern analysis to the ECG data. The pattern analysis identifies whether there are certain patterns among multiple leads that would indicate the presence of an AMI. In decision block 108, if AMI is detected, then the component returns an indication that AMI is present, else the component continues at block 109. In block 109, the component generates an AMI score. In decision block 110, if the AMI score indicates the presence of an AMI, then the component returns an indication that AMI is present, else the component returns an indication that no AMI is present.

Figure 2:
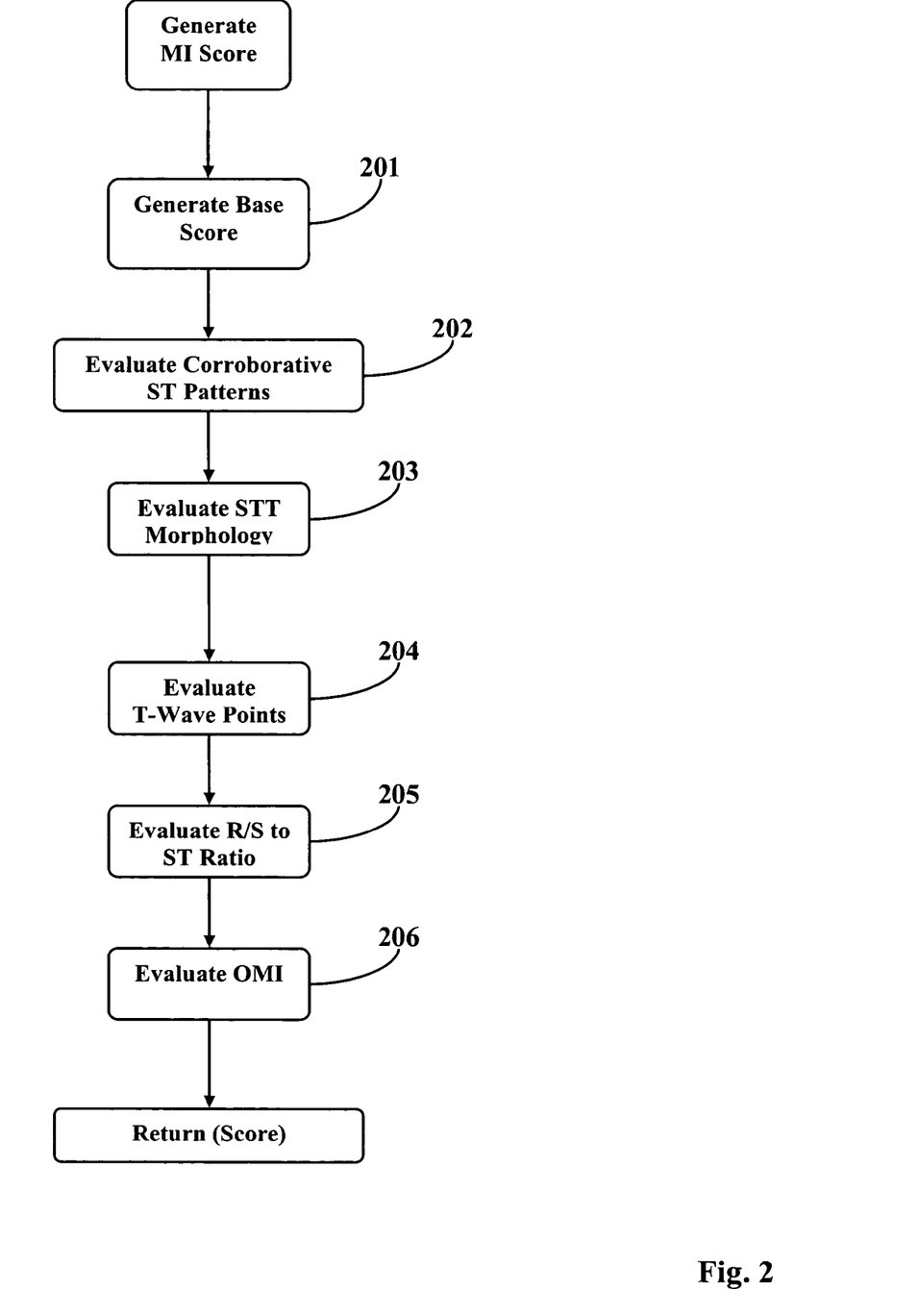

FIG. 2 is a flow diagram illustrating the processing of the generate AMI score in one embodiment. In block 201, the component generates a base AMI score. The base AMI score is based on a ratio of ST elevation and depression to a threshold value. In blocks 202–206, the component adjusts the base AMI score to account for evidence that may tend to indicate the presence or absence of an AMI, which tend to affect the detection of borderline AMI. In block 202, the component evaluates corroborative ST patterns and increases the AMI score accordingly. For example, if the ST deviation is pathological, then the component may increase the base score when ST elevation is present in V1 or V4. In block 203, the component evaluates STT morphology and adjusts the AMI score. The STT morphology may increase or decrease the AMI score based on shape, concavity, and slope of the STT data. In block 204, the component evaluates T-wave points and adjusts AMI score. In block 205, the component evaluates the ratio of R/S in relation to the ST ratio and adjusts the AMI score. In block 206, the component evaluates the presence of an OMI and decreases the AMI score. The component then returns an indication of the AMI score.

The AMI system outputs a statement that indicates that AMI is present, probably present, probably not present, or not present.

Old Myocardial Infarction

Figure 3:
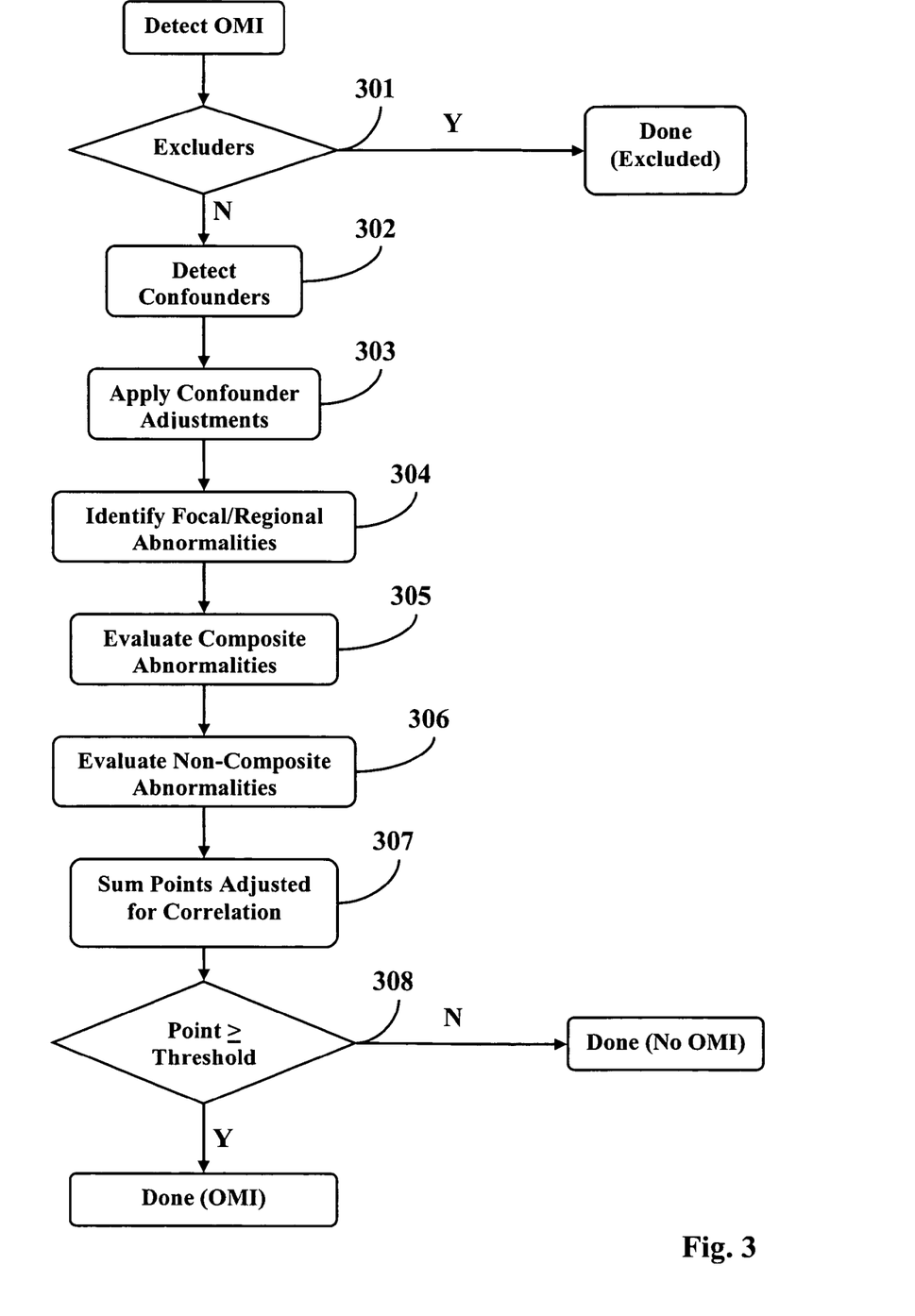

FIG. 3 is a flow diagram illustrating the processing of the detect OMI component in one embodiment. Indecision block 301, if the patient has an excluding condition, then the component completes, else the component continues at block 302. In block 302, the component detects confounding conditions in the patient. These confounding conditions may include LVH, RVH, LBBB, RBBB, and LAFB. The component identifies characteristics that look like these confounding conditions that may impact the OMI detection. In block 303, the component adjusts to account for the detected confounding conditions. The component may inhibit criteria that may not be reliable because of the confounding conditions and may normalize ECG to remove the effects of the confounding conditions. In blocks 304–307, the component implements gender-specific algorithms to detect OMI. In block 304, the component identifies focal and regional abnormalities in the patient. A focal abnormality is based on a single lead, while a regional abnormality is based on multiple leads. Abnormalities that occur during the polarization and repolarization are both identified. In block 305, the component evaluates the composite abnormalities. The evaluation is based on comparing abnormalities detected from analysis of both regional depolarization and repolarization, both focal depolarization and regional depolarization, and focal depolarization and repolarization. In block 306, the component evaluates composite abnormalities. The composite abnormalities are regional depolarization abnormalities and focal depolarization abnormalities. In block 307, the component adds the points resulting from the evaluations. The component adjusts the points to account for correlation between the points. In decision block 308, if the total points is greater than or equal to an OMI threshold, then the component returns an indication that OMI is present, else the component returns an indication that OMI is not present.

Figure 4:
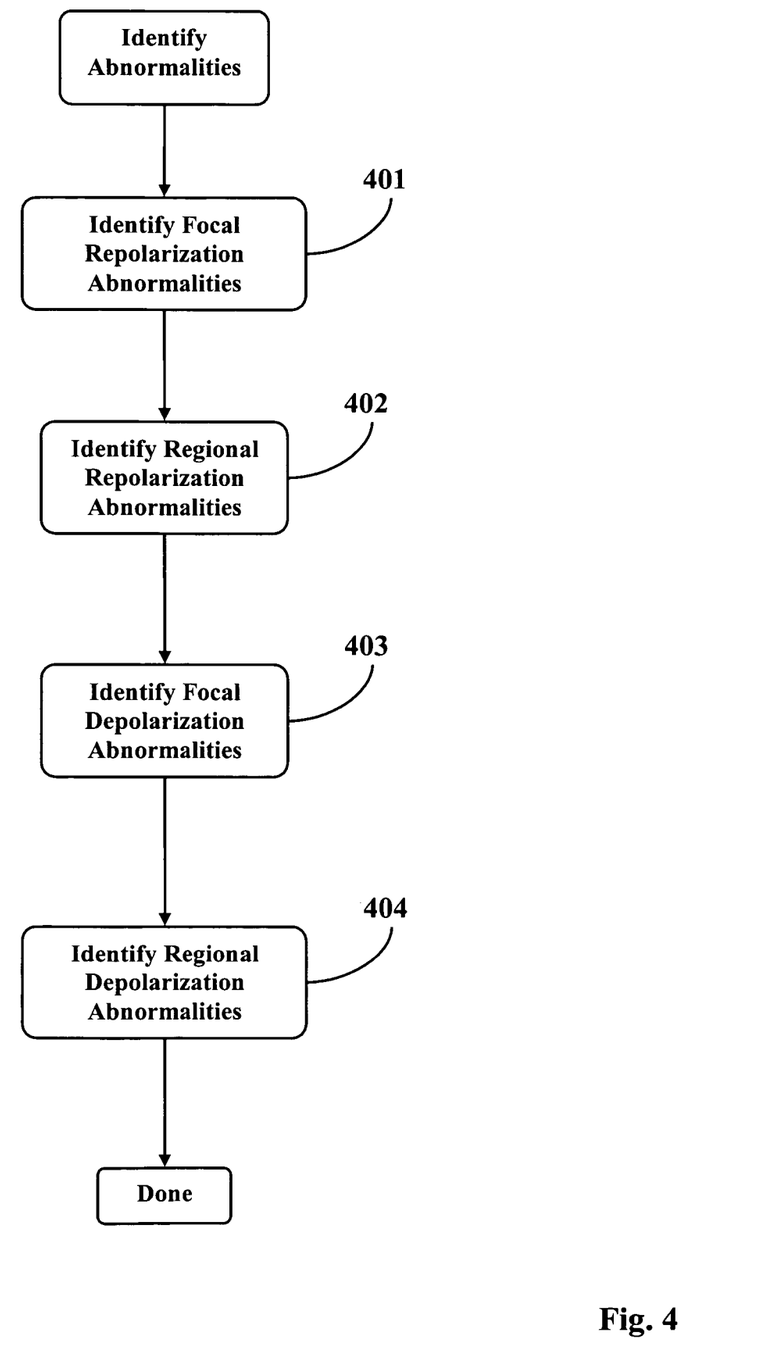

FIG. 4 is a flow diagram illustrating the processing of the identify abnormalities component in one embodiment. In block 401, the component identifies focal repolarization abnormalities. In block 402, the component identifies regional repolarization abnormalities. In block 403, the component identifies focal depolarization abnormalities. In block 404, the component identifies regional depolarization abnormalities and then completes.

Figure 5:
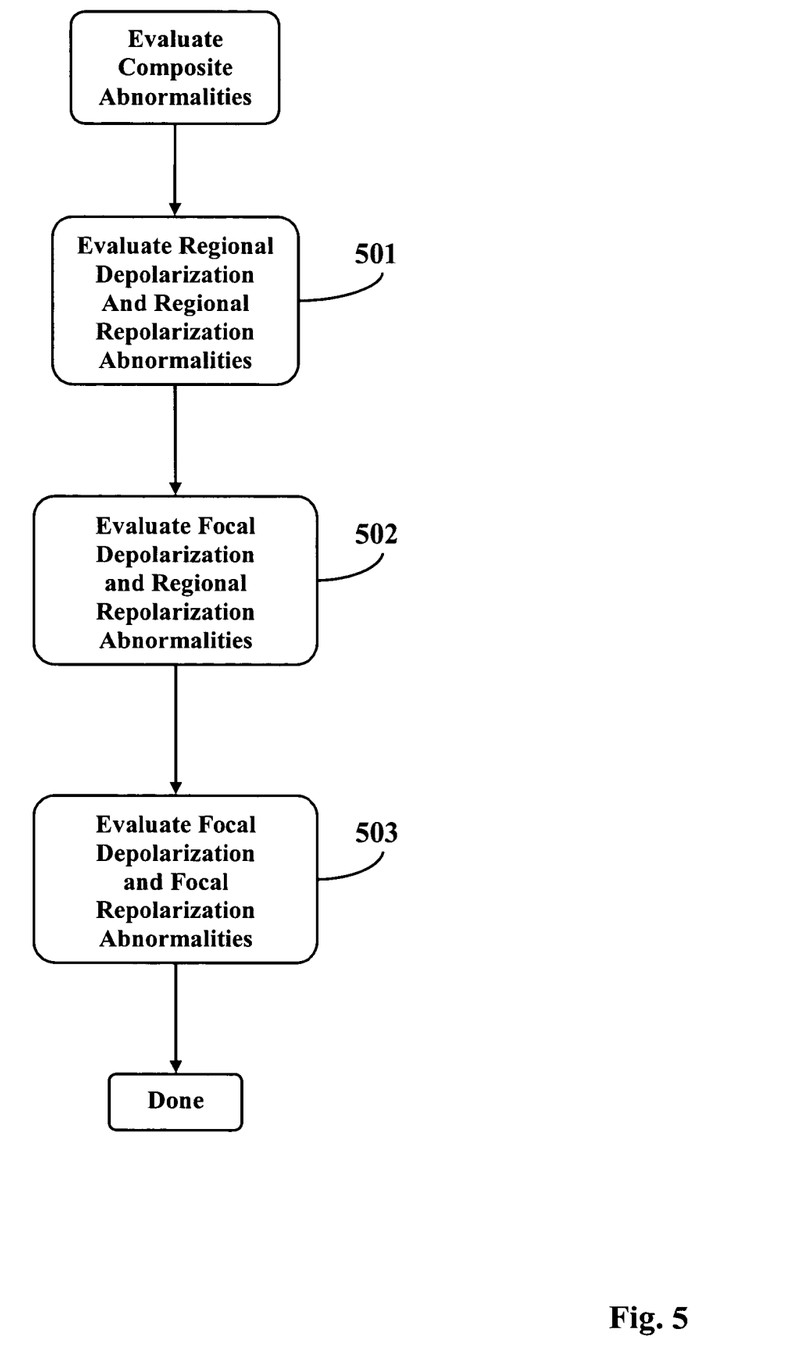

FIG. 5 is a flow diagram illustrating the processing of the evaluate composite abnormalities component in one embodiment. In block 501, the component evaluates the regional depolarization abnormalities taking into consideration the regional repolarization abnormalities. In block 502, the component evaluates the focal depolarization taking into consideration the regional repolarization abnormalities. In block 503, the component evaluates focal depolarization abnormalities taking into consideration the focal repolarization abnormalities. The component then completes.

Figure 6:
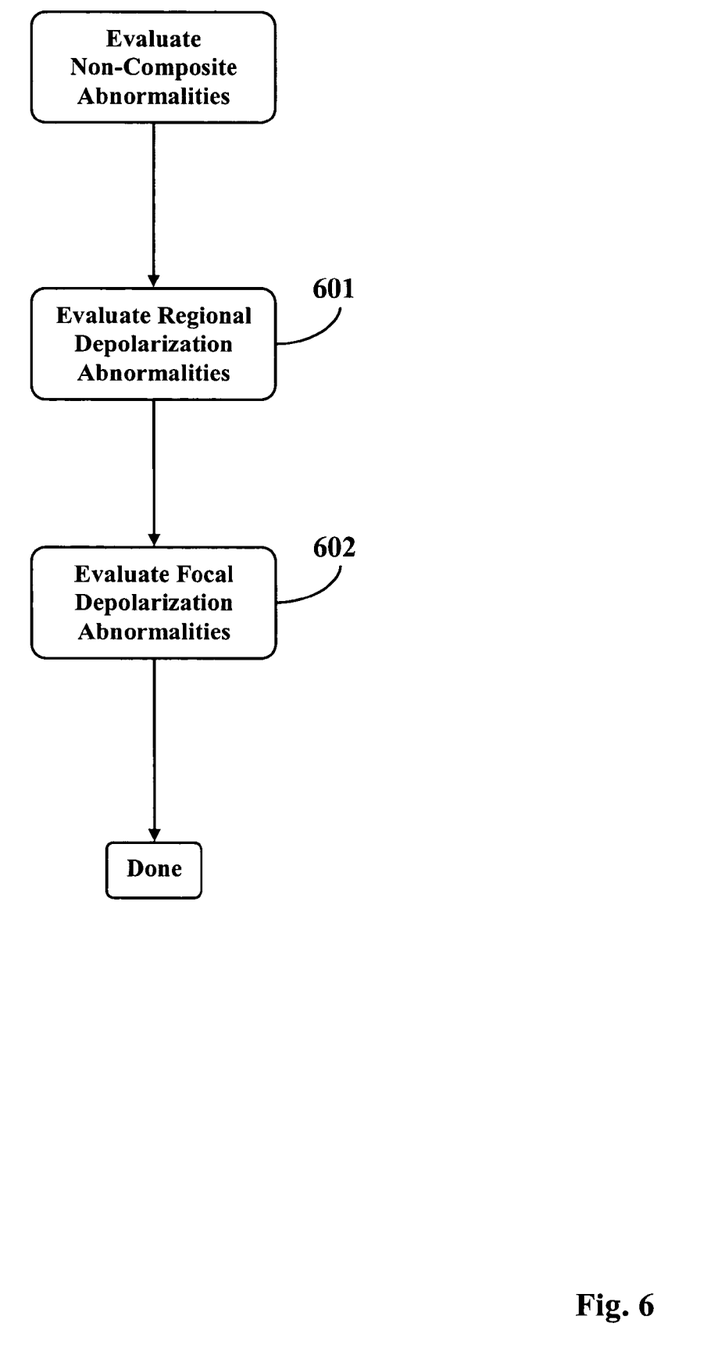

FIG. 6 is a flow diagram illustrating processing of the evaluate non-composite abnormalities component in one embodiment. In block 601, the component evaluates regional depolarization abnormalities. In block 602, the component evaluates focal depolarization abnormalities. The component then completes.

Figure 7:
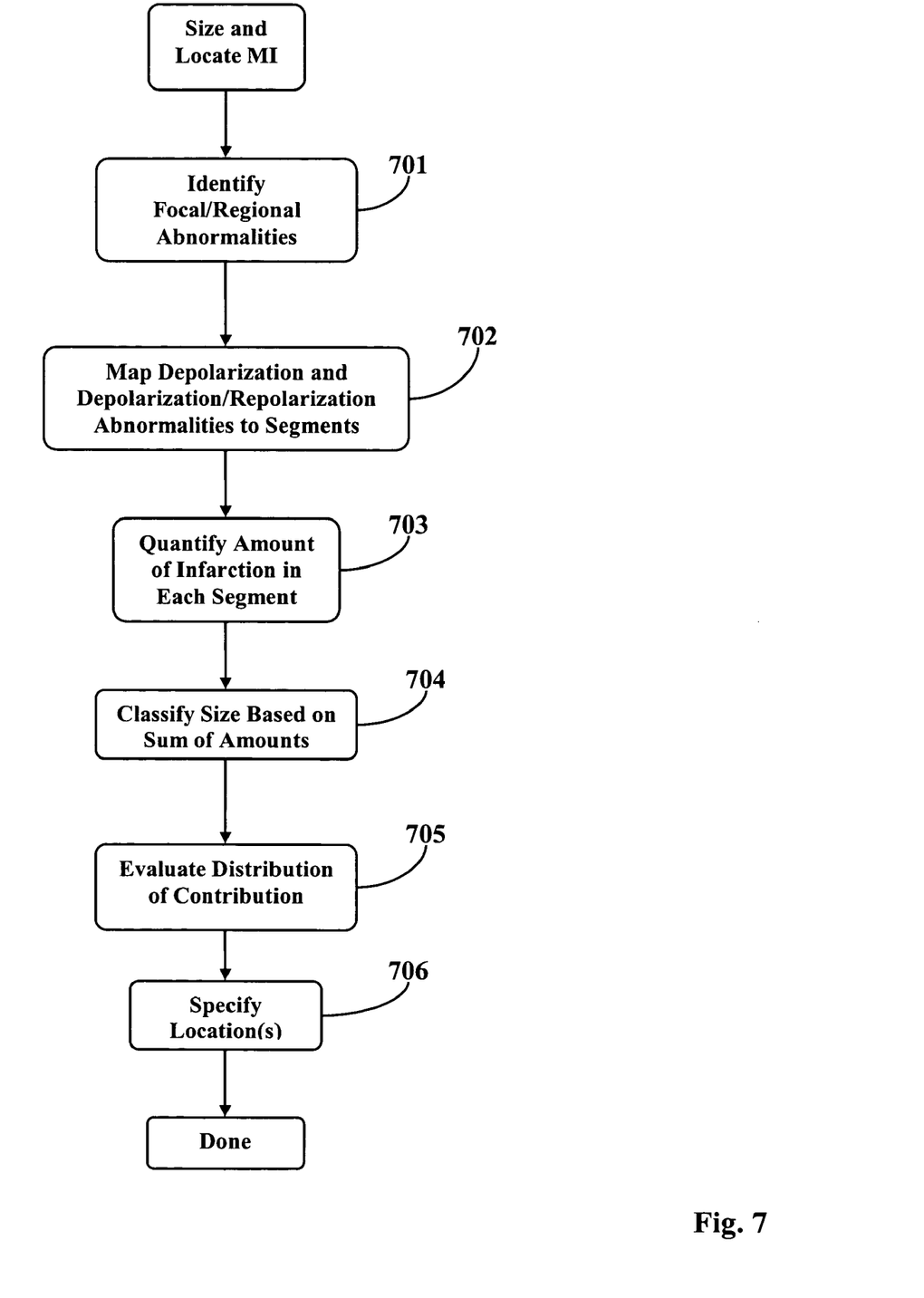

FIG. 7 is a flow diagram illustrating the processing of the size and locate MI component in one embodiment. In block 701, the component identifies the focal and regional abnormalities. In block 702, the component maps the depolarization abnormalities and the depolarization and repolarization abnormalities into segments of the left ventricle. In block 703, the component quantifies the amount of infarction in each segment. The amount in each segment can either be zero, three, or six percent. In block 704, the component classifies the size of the infarction based on the sum of the amounts. For example, a small infarction is between 3 and 15%, a medium infarction is between 6 and 25%, and a large infarction is greater than 25%. In block 705, the component evaluates the distribution of the contribution. This information is used by the AMI detection component to determine the effect of the OMI on the AMI. In block 706, the component specifies the locations of the OMI. The component then completes.

Figure 8:
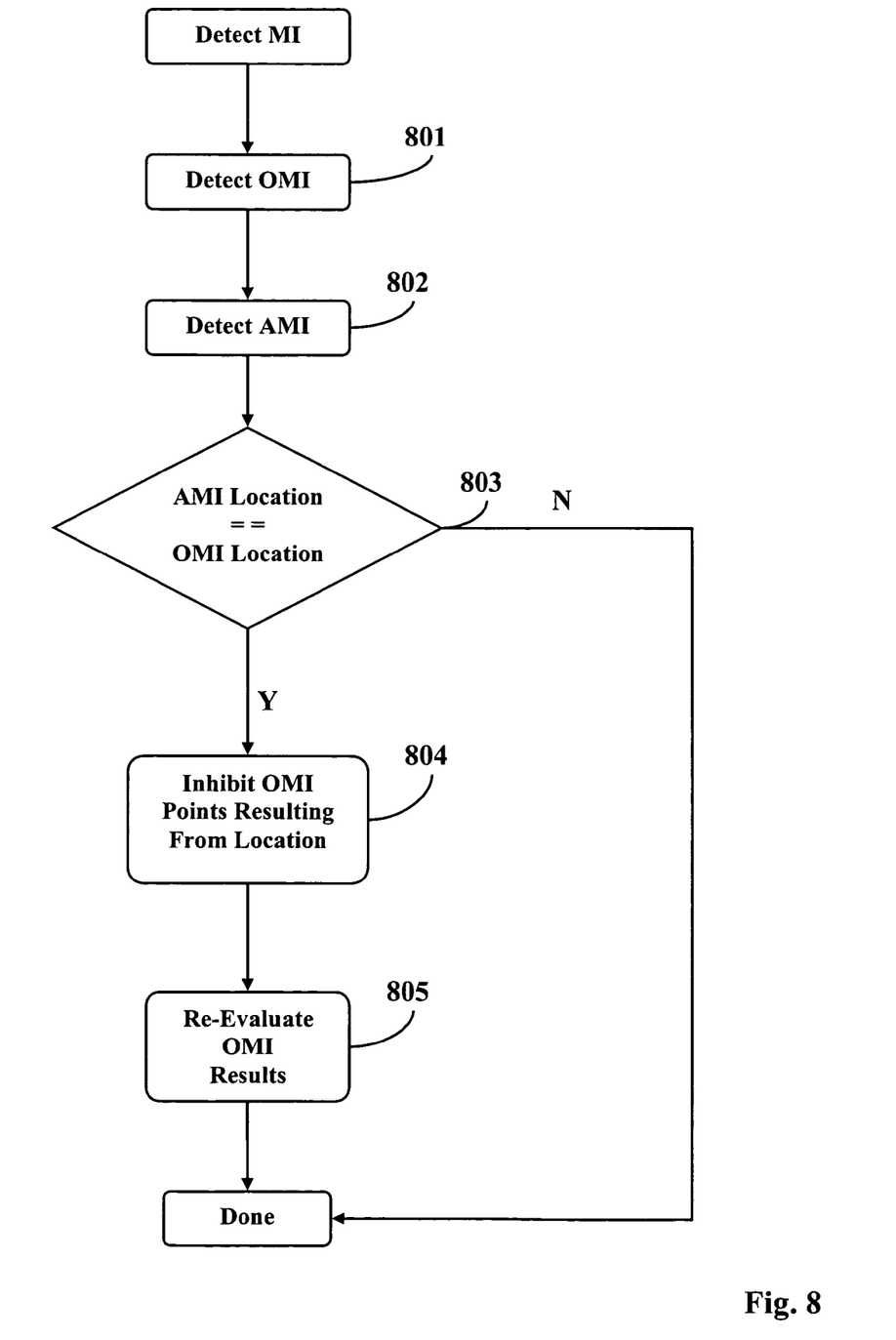

FIG. 8 is a flow diagram illustrating processing of the overall detect MI component in one embodiment. In block 801, the component detects OMI. In block 802, the component detects AMI. The detection of the AMI uses information provided by the detection of OMI. In decision block 803, if the AMI location equals an OMI location, then the component continues at block 804, else the component completes. In block 804, the component inhibits the OMI points that resulted from the AMI location. In block 805, the component reevaluates the OMI results based on the inhibited points. The component then completes.

We claim:

1. A method utilizing ECG data and a computer system for detecting myocardial infarction in a patient's heart comprising receiving from that patient ECG data which includes ST data, examining such included ST data to detect whether it indicates the presence of an ST deviation, as a result of said examining, and if such an ST deviation is detected, analyzing the ST deviation to determine whether it is a benign or a non-benign deviation, if the ST deviation is determined to be non-benign, implementing a selected pathological thresholding step, following said implementing, normalizing the detected and determined non-benign ST deviation data, after performing said normalizing, applying selected pattern analysis to the normalized, non-benign ST deviation data, and after said applying, generating a score indicating the yes/no presence of a myocardial infarction.

\* \* \* \* \*